United States Patent [19]

Monbaliu et al.

[11] 4,000,156
[45] Dec. 28, 1976

[54] PREPARATION OF 4-METHYL-2-PYRAZOLIN-5-ONES

[75] Inventors: Marcel Jacob Monbaliu, Mortsel, Belgium; Walter Püschel, Leverkusen, Germany; Raphaël Karel Van Poucke, Berchem, Belgium

[73] Assignee: AGFA-GEVAERT N.V., Mortsel, Belgium

[22] Filed: May 30, 1975

[21] Appl. No.: 582,225

[30] Foreign Application Priority Data

June 12, 1974 Germany .......................... 2428431

[52] U.S. Cl. .................................. 260/310 A
[51] Int. Cl.² ................................ C07D 231/08
[58] Field of Search ........................ 260/310 A

[56] References Cited

FOREIGN PATENTS OR APPLICATIONS

| 2,304,319 | 8/1974 | Germany | 260/310 A |
|---|---|---|---|
| 386,918 | 1/1933 | United Kingdom | 260/310 A |

*Primary Examiner* — Donald B. Moyer
*Attorney, Agent, or Firm* — A. W. Breiner

[57] ABSTRACT

A method is described for the preparation of a 1-substituted 4-methyl-2-pyrazolin-5-one by catalytic hydrogenation under pressure and simultaneous methylation by means of paraformaldehyde of the appropriate 1-substituted 2-pyrazolin-5-one in a medium of an inert organic solvent comprising ammonium acetate.

10 Claims, No Drawings

PREPARATION OF 4-METHYL-2-PYRAZOLIN-5-ONES

The present invention relates to a novel method for the preparation of 4-methyl-2-pyrazolin-5-ones.

It is known that for the manufacture of a photographic colour image in a light-sensitive silver halide emulsion layer, the exposed silver halide is developed to a silver image by means of an aromatic primary amino compound in the presence of a colour coupler which by reaction with the oxidized developer forms a dye on the areas corresponding to the silver image.

In the subtractive three-colour photography usually a light-sensitive photographic colour material is used comprising a red-sensitized, a green-sensitized and a blue-sensitive silver halide emulsion layer wherein on development by means of suitable colour couplers a cyan, a magenta and a yellow dye image are formed respectively.

For the formation of the magenta separation image it is known to use 2-pyrazolin-5-one compounds yielding on colour development magenta azomethine dyes.

It is also known, in order to improve colour reproduction in photographic silver halide colour elements, to incorporate therein so-called competing couplers which react with the oxidation products of aromatic primary amino colour developing agents to form colourless compounds. These competing couplers are used in those instances where undesirable oxidation products of the developing agents should be rendered ineffective so that degradation of the colour image quality is inhibited.

It is known to use as competing couplers 2-pyrazolin-5-one compounds which differ from the magenta-forming 2-pyrazolin-5-one colour couplers in that the reactive methylene group in the 4-position carries an alkyl group, more particularly a methyl group.

4-Methyl-2-pyrazolin-5-one competing couplers can thus be represented by the following general formula I:

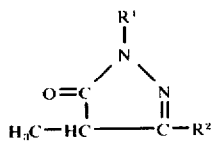

wherein:

$R^1$ represents a substituent of the type well known in the 1-position of 2-pyrazolin-5-one colour couplers e.g. alkyl, especially $C_1-C_5$-alkyl, which may be substituted e.g. by fluoro such as 2-trifluoroethyl, cyano such as 2-cyanoethyl and aryl such as benzyl and substituted benzyl, or preferably aryl, e.g. phenyl which may be substituted e.g. phenyl substituted by alkyl such as methyl, halogen such as chlorine and bromine, sulpho, alkoxy such as methoxy, alkylsulphonyl such as methylsulphonyl, alkylthio such as methylthio, haloalkyl, haloalkylthio, haloalkylsulphonyl, etc., $R^2$ represents any of the groups present in the 3-position of prior art 2-pyrazolin-5-one colour couplers including e.g. an alkyl group, an aryl group, a heterocyclic group, an arylamino group or an acylamino group e.g. -NHCO-alkyl, -NHCO-aryl, -NHCO-aralkyl, -NHCONH-alkyl, -NHCONH-aryl, -NHCONH-aralkyl, alkoxycarbonylamino, aryloxycarbonylamino, and aralkyloxycarbonylamino.

The 4-methyl-2-pyrazolin-5-one competing couplers carrying in the 3-position an alkyl, aryl or heterocyclic group can be prepared by cyclisation of the appropriate N-monosubstituted hydrazine with an α-acylpropionic acid ester (see e.g. Belgian Pat. No. 560,907) whereas those carrying in the 3-position an arylamino group or an acylamino group can be prepared from the corresponding 3-amino-4-methyl-2-pyrazolin-5-ones which in their turn can be prepared by cyclisation of the appropriate N-monosubstituted hydrazine with α-methyl-β-imino-β-ethoxypropionic acid ethyl ester (see e.g. German Pat. No. 884,151, U.S. Pat. Nos. 3,325,482 and 3,470,191 and UK Pat. No. 1,264,477).

The method according to which the 3-amino-4-methyl-2-pyrazolin-5-one compounds and derivatives are prepared, which can be represented by the following reaction scheme:

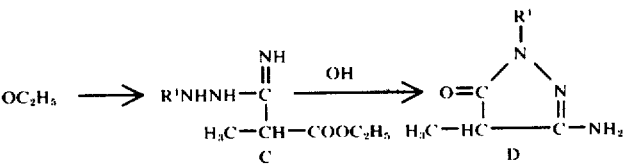

has several disadvantages. When the condensation is carried on a technical scale special measures have to be taken owing to the instability of compound B against moisture and the susceptibility to oxidation of the intermediate reaction product C. Moreover compound B is prepared from the noncommercially available α-cyanopropionic acid ethyl ester which should be made by reaction of a cyanide, e.g. potassium cyanide, with α-halo- (e.g. α-chloro-)-propionic acid ethyl ester. The latter reaction has low yields and requires heavy safety precautions owing to liberation of hydrogen cyanide.

In order to avoid these disadvantages it would be highly desirable to succeed in directly methylating the 3-amino-2-pyrazolin-5-one compound. 3-Amino-2-pyrazolin-5-ones are well known intermediate compounds for use in the preparation of magenta-forming 2-pyrazolin-5-one colour couplers and can be prepared as is known in the art by cyclisation of the appropriate N-monosubstituted hydrazine with β-imino-β-ethoxypropionic acid ethyl ester. The latter compound is stable against moisture and is prepared from the commercially available α-cyanoacetic acid ethyl ester.

However, experiments for directly methylating the 3-amino-2-pyrazolin-5-ones in their salt form e.g. magnesium or sodium salt, by means of known alkylating agents e.g. methyl iodide and dimethyl sulphate were not successful. In addition to the desired 4-methyl-3-amino-2-pyrazolin-5-one various by-products were formed such as 4,4-dimethylpyrazolinone and 5-methyloxypyrazolinone, which are hard to remove.

It has now been found that 1-substituted 4-methyl-2-pyrazolin-5-ones can be prepared by simultaneous catalytic hydrogenation under pressure and methylation by means of paraformaldehyde of the appropriate 1-substituted 2-pyrazolin-5-one in a medium of an inert organic solvent, e.g. dioxan, ethylene glycol monoalkyl ethers such as the monomethyl ether, and preferably $C_1$–$C_5$ alcohol e.g. methanol and ethanol, comprising ammonium acetate.

The method of the invention is particularly valuable for the preparation of 1-substituted 4-methyl-2-pyrazolin-5-one competing couplers carrying in the 3-position an arylamino or acylamino group as referred to hereinbefore for the reasons set forth above.

The 3-amino-2-pyrazolin-5-ones can be converted into the 3-arylamino- and 3-acylamino-derivatives according to known methods as described, e.g., in German Pat. No. 884,151, U.S. Pat. Nos. 3,325,482 and 3,470,191 and UK Pat. No. 1,264,477 before or after methylation in accordance with the method of the present invention.

When in the method of the invention 2-pyrazolin-5-ones with free amino group in the 3-position are methylated, sometimes rather low yields are obtained probably owing to reaction of the free amino group with formaldehyde. In these instances, it may be interesting to block the free amino groups before methylation e.g. by converting it into an alkoxycarbonylamino group such as ethoxycarbonylamino group. After methylation, the compound is again converted into its free amino form by hydrolysis. This is illustrated by the following reaction scheme:

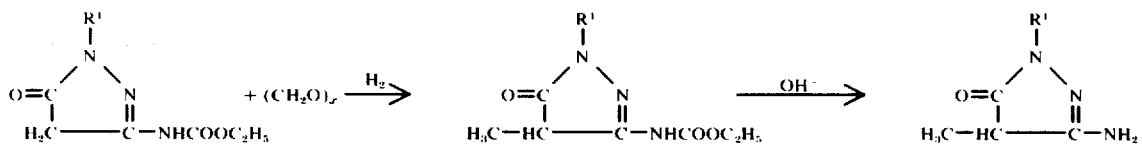

The methylation reaction according to the present invention is generally carried out under a hydrogen pressure of about 300 to about 1500 psi. In most cases, the hydrogen is readily absorbed at temperatures comprised between about 75° and 125° C.

Hydrogenation catalysts are well known in the art of organic chemistry for which there can be referred to Ullmanns Enzyklopädie der technischen Chemie, Vol. 9, pp. 254 ff. and Vol. 14, pp. 640 ff which include noble and base metal catalysts. Raney nickel is the preferred catalyst but other catalysts of the platinum metal series can be used which include platinum, palladium, rhodium, ruthenium and rhenium catalysts e.g. palladium black, palladium on charcoal, platinum on charcoal, platinum sponge, platinum black, etc.

The paraformaldehyde is generally used in amounts varying from about 1.5 to about 3.5 moles per mole of 2-pyrazolin-5-one and the ammonium acetate is generally used in amounts varying from about 1 to about 3 moles per mole of 2-pyrazolin-5-one.

The following preparations illustrate the method of the present invention.

PREPARATION 1

1-(p-methylsulphonylphenyl)-3-amino-4-methyl-2-pyrazolin-5-one.

In a 3 liter autoclave were placed: 151.8 g (0.6 mole) of 1-(p-methylsulphonylphenyl)-3-amino-2-pyrazolin-5-one, 27 g (0.9 mole) of paraformaldehyde, 115.5 g (1.5 mole) of ammonium acetate, 60 g of Raney nickel and 1735 ml of methanol. The autoclave was charged with hydrogen to a pressure of 1500 psi. After reduction for 2 h at 100° C the catalyst was filtered off and the filtrate was neutralized by addition of 100 ml of concentrated hydrochloric acid. The filtrate was concentrated by evaporation and the residue was diluted by addition of 300 ml of water. The precipitate was separated and treated with boiling acetonitrile. Yield: 65 g (40%). Melting Point: 239°–240° C.

PREPARATION 2

1-phenyl-3-(α-sulphostearoylamino)-4-methyl-2-pyrazolin-5-one

An autoclave was charged with 52.1 g (0.1 mole) of 1-phenyl-3-(α-sulphostearoylamino)-2-pyrazolin-5-one, 15.4 g (0.2 mole) of ammonium acetate, 4.5 g (0.15 mole) of paraformaldehyde, 10 g of Raney nickel and 535 ml of ethanol. The mixture was heated to 75° C whereupon hydrogenation started at a hydrogen pressure of 700 psi. After 30 min the hydrogen pressure was released and another 4.5 g of paraformaldehyde were added whereupon hydrogenation was continued. After having filtered off the catalyst, the filtrate was acidified with 100 ml of concentrated hydrochloric acid. The precipitate was filtered off. Yield: 41 g (75%). Melting point: 240° C.

PREPARATION 3

1-phenyl-3-amino-4-methyl-2-pyrazolin-5-one a. 1-phenyl-3-carbethoxyamino-4-methyl-2-pyrazolin-5-one.

1. A 3 liter autoclave was charged with 296.4 g (1.2 mole) of 1-phenyl-3-carbethoxyamino-2-pyrazolin-5-one (J. Am. Chem. Soc. 64, 2133-2136, 1942), 92.4 g (1.2 mole) of ammonium acetate, 54 g (1.8 mole) of paraformaldehyde, 60 g of Raney nickel and 1450 ml of methanol.

The autoclave was charged with hydrogen to a pressure of 650 psi and rapidly heated to 80° C. With agitating the temperature was raised to 100° C and when the pressure had dropped to 300 psi it was raised again to 670 psi.

After about 30 min the theoretical amount of hydrogen was absorbed whereupon the reaction mixture was cooled to 40° C and the catalyst was filtered off. The filtrate was neutralized by means of 100 ml concentrated hydrochloric acid and diluted with 4 l of water. The crystalline product was separated and dried. Yield: 270 g (86%). Melting point: 136° C.

2. Step (1) was completely repeated by using the same reaction conditions and concentrations but with the only difference that the Raney nickel was replaced by 3 g of palladium on charcoal. The hydrogenation time was about 1 h. Yield: 251 g (80%). Melting point: 136° C.

b. 1-phenyl-3-amino-4-methyl-2-pyrazolin-5-one

A solution of 261 g (1 mole) of 1-phenyl-3-carbethoxyamino-4-methyl-2-pyrazolin-5-one in 1600 ml of 2.5 N sodium hydroxide was refluxed for 30 min. The solution was cooled and neutralized by addition of 250 ml of concentrated hydrochlorid acid and 50 ml of glacial acetic acid. The precipitate was separated and dried. Yield: 160 g (84%). Melting point: 147° C.

PREPARATION 4

1-(m-chlorophenyl)-3-amino-4-methyl-2-pyrazolin-5-one a.

1-(m-chlorophenyl)-3-carbethoxyamino-2-pyrazolin-5-one.

209.5 g (1 mole) of 1-(m-chlorophenyl)-3-amino-2-pyrazolin-5-one were dissolved at 70° C in a solution of 89 g (0.66 mole) of anhydrous aluminium chloride in 1000 ml of acetonitrile, and 250 ml of pyridine were added. Then 119.5 g of ethyl chloroformiate were added dropwise at 80° C whereupon the mixture was refluxed for 1 h. The mixture was cooled to 50° C, diluted with 500 ml of methanol and acidified with 100 ml of concentrated hydrochloric acid. The precipitate was filtered off, stirred with methanol and dried. Yield: 163 g (58%). Melting point: 189° C.

b.

1-m-chlorophenyl-3-carbethoxyamino-4-methyl-2-pyrazolin-5-one.

112.6 g (0.4 mole) of 1-m-chlorophenyl-3-carbethoxyamino-2-pyrazolin-5-one were methylated under hydrogen atmosphere by using 20 g of Raney nickel, 46.2 g (0.6 mole) of ammonium acetate, 27 g (0.9 mole) of paraformaldehyde, and 0.9 mole of hydrogen in a total volume of 600 ml of methanol. Hydrogenation occurred at a pressure interval of 700 to 300 psi at a temperature of 80°-100° C. Yield: 74 g (62%). Melting point: 162° C.

c.

1-m-chlorophenyl-3-amino-4-methyl-2-pyrazolin-5-one.

A solution of 69 g (0.2 mole) of 1-m-chlorophenyl-3-carbethoxyamino-4-methyl-2-pyrazolin-5-one in 320 ml of 2.5 N sodium hydroxide was refluxed for 30 min. The solution was cooled and neutralized by addition of glacial acetic acid. The precipitate was dried under reduced pressure. Yield: 39 g (87%). Melting point: 138° C.

PREPARATIONS 5-8

The compounds corresponding to the following formula:

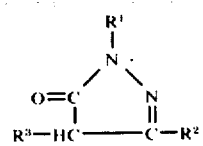

and listed in the following table were prepared according to the methods of preparation 4.

Table

| $R^1$ | $R^3$ | $R^2$ | Yield (%) | Melting point (° C) |
|---|---|---|---|---|
| 2,3,4-trichlorophenyl (Cl, Cl, Cl) | H | NHCOOC$_2$H$_5$ | 78 | 248 |
|  | CH$_3$ | NHCOOC$_2$H$_5$ | 23 | 210 |
|  | CH$_3$ | NH$_2$ | 75 | 291 |
| H$_3$CSO$_2$-C$_6$H$_4$- | H | NHCOOC$_2$H$_5$ | 62 | 235 |
|  | CH$_3$ | NHCOOC$_2$H$_5$ | 53 | 211 |
|  | CH$_3$ | NH$_2$ | 60 | 248 |
| C$_6$H$_5$-CH$_2$- | H | NHCOOC$_2$H$_5$ | 27 | 190 |
|  | CH$_3$ | NHCOOC$_2$H$_5$ | 80 | 152 |
|  | CH$_3$ | NH$_2$ | 83 | 143 |
| CF$_3$CH$_2$- | H | NHCOOC$_2$H$_5$ | 69 | 189 |
|  | CH$_3$ | NHCOOC$_2$H$_5$ | 41 | 130 |
|  | CH$_3$ | NH$_2$ | 70 | 129 |

We claim:
1. In the method for the preparation of a 1-substituted 4-methyl-2-pyrazolin-5-one which comprises catalytic hydrogenation under pressure and simultaneous methylation of a 1-substituted 2-pyrazolin-5-one having the formula

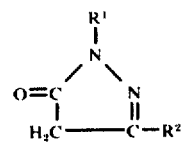

wherein:
R$^1$ represents an alkyl group or an aryl group, and
R$^2$ represents an alkyl group, an aryl group, a heterocycle, or an amino group,
the improvement wherein the reagents include paraformaldehyde in a medium of an inert organic solvent comprising ammonium acetate.

2. Method according to claim 1, wherein R$^2$ is an amino group.

3. Method according to claim 1, wherein R$^2$ is an alkoxycarbonylamino group.

4. Method according to claim 1, wherein the hydrogenation occurs at a hydrogen pressure comprised between about 300 and about 1500 psi.

5. Method according to claim 1, wherein hydrogenation occurs at a temperature comprised between about 75° and about 125° C.

6. Method according to claim 1, wherein the amount of paraformaldehyde is comprised between about 1.5 and about 3.5 moles per mole of 2-pyrazolin-5-one.

7. Method according to claim 1, wherein the amount of ammonium acetate is comprised between about 1 and about 3 moles per mole of 2-pyrazolin-5-one.

8. Method according to claim 1, wherein the hydrogenation catalyst is Raney nickel.

9. Method according to claim 1, wherein the inert organic solvent is a $C_1$–$C_5$ alcohol.

10. Method according to claim 9, wherein the inert organic solvent is methanol or ethanol.

* * * * *